United States Patent
Schara et al.

(10) Patent No.: US 7,896,803 B2
(45) Date of Patent: Mar. 1, 2011

(54) VARIABLE DIRECTION OF VIEW INSTRUMENT WITH ON-BOARD ACTUATORS

(75) Inventors: Nathan Jon Schara, Pasadena, CA (US); Hans David Hoeg, Arcadia, CA (US); Eric L. Hale, Altadena, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 751 days.

(21) Appl. No.: 11/352,644

(22) Filed: Feb. 13, 2006

(65) Prior Publication Data

US 2006/0206006 A1    Sep. 14, 2006

Related U.S. Application Data

(60) Provisional application No. 60/652,984, filed on Feb. 14, 2005.

(51) Int. Cl.
*A61B 1/00* (2006.01)

(52) U.S. Cl. .......... 600/173; 600/130; 600/137; 600/170

(58) Field of Classification Search .................. 600/117, 600/118, 130, 137, 139, 170, 173
See application file for complete search history.

(56) References Cited

U.S. PATENT DOCUMENTS

| | | | | |
|---|---|---|---|---|
| 3,773,039 A | * | 11/1973 | Mori et al. | 600/173 |
| 3,856,000 A | | 12/1974 | Chikama | 128/6 |
| 3,880,148 A | * | 4/1975 | Kanehira et al. | 600/173 |
| 4,503,842 A | * | 3/1985 | Takayama | 600/152 |
| 4,697,577 A | | 10/1987 | Forkner | 128/6 |
| 5,471,988 A | * | 12/1995 | Fujio et al. | 600/439 |
| 5,575,754 A | * | 11/1996 | Konomura | 600/117 |
| 5,762,603 A | * | 6/1998 | Thompson | 600/112 |
| 5,782,752 A | * | 7/1998 | Lichtman et al. | 600/137 |
| 5,935,057 A | * | 8/1999 | Lichtman et al. | 600/137 |
| 6,097,423 A | | 8/2000 | Mattsson-Boze et al. | 348/65 |
| 6,371,909 B1 | * | 4/2002 | Hoeg et al. | 600/173 |
| 6,398,725 B1 | * | 6/2002 | Thompson | 600/173 |

(Continued)

FOREIGN PATENT DOCUMENTS

EP    299 07 430    10/1999

(Continued)

OTHER PUBLICATIONS

European Search Report; May 30, 2006; 10 pages.

*Primary Examiner* — John P Leubecker
*Assistant Examiner* — Samuel Candler
(74) *Attorney, Agent, or Firm* — St. Onge Steward Johnston & Reens LLC (57) ABSTRACT

A viewing instrument with a variable direction of view is disclosed generally comprising an outer instrument shaft, such as endoscope shaft, with a viewing element at its distal end, and an inner drive shaft within the outer shaft for moving the viewing element in order to change the direction of the view vector. First and second on-board actuators, such as motors, are arranged in the proximal portion of the instrument for rotating the outer and inner shaft, respectively, in order to rotate the viewing element through two degrees of freedom. In certain embodiments, the axes of the shafts are coincident, and the viewing element rotates about a rotational axis substantially perpendicular to shaft axes. In some embodiments, the axes of the motors are substantially parallel.

20 Claims, 6 Drawing Sheets

U.S. PATENT DOCUMENTS

| | | | |
|---|---|---|---|
| 6,428,470 B1 * | 8/2002 | Thompson | 600/173 |
| 6,500,115 B2 | 12/2002 | Krattiger et al. | 600/173 |
| 6,648,817 B2 * | 11/2003 | Hale et al. | 600/173 |
| 6,663,559 B2 | 12/2003 | Hale et al. | 600/118 |
| 6,797,931 B2 * | 9/2004 | Iizuka et al. | 250/201.3 |
| 7,517,314 B2 * | 4/2009 | Hoeg et al. | 600/117 |
| 2001/0008952 A1 * | 7/2001 | Takada | 600/155 |
| 2002/0040217 A1 * | 4/2002 | Jinno | 606/1 |
| 2002/0099263 A1 * | 7/2002 | Hale et al. | 600/117 |
| 2002/0103420 A1 | 8/2002 | Coleman et al. | 600/173 |
| 2002/0133077 A1 | 9/2002 | Edwardsen et al. | 600/462 |
| 2003/0032862 A1 * | 2/2003 | Ota et al. | 600/158 |
| 2003/0092966 A1 | 5/2003 | Schara et al. | 600/173 |
| 2004/0015049 A1 | 1/2004 | Zaar | 600/101 |

FOREIGN PATENT DOCUMENTS

| | | |
|---|---|---|
| EP | 1166710 A2 | 1/2002 |
| EP | 1 481 627 | 12/2004 |
| JP | 2002000550 A | 1/2002 |
| WO | WO 01/22865 A1 | 4/2001 |

* cited by examiner

VARIABLE DIRECTION OF VIEW INSTRUMENT WITH ON-BOARD ACTUATORS

CROSS-REFERENCE TO RELATED APPLICATIONS

This patent application claims the benefit of, under Title 35, United States Code, Section 119(e), U.S. Provisional Patent Application No. 60/652,984, filed Feb. 14, 2005.

FIELD OF THE INVENTION

The present invention relates to an on-board actuation system for a viewing instrument, such as an endoscope. More specifically, the invention relates to an instrument with a variable direction of view having on-board actuators for causing the rotations necessary to provide the view vector with at least two degrees of freedom.

BACKGROUND OF THE INVENTION

Viewing instruments, such as endoscopes, are generally well known in the art. Generally, an endoscope is a medical device for insertion into a body passageway or cavity that enables an operator to view and/or perform certain surgical procedures at a site inside a patient's body. As is known, endoscopes may be either rigid or flexible, and generally include a long tubular member equipped with, for example, some type of system for transmitting images to the user, and in some cases, a working channel for a surgical instrument. The endoscope has a proximal end that remains external to the patient, from which the operator can view the site and/or manipulate a surgical instrument, and a distal end having an endoscope tip for insertion into the body cavity of the patient.

Numerous variable direction of view endoscopes have been proposed, such as the swing prism designs disclosed in U.S. Pat. No. 3,856,000 to Chikama et al., U.S. Pat. No. 4,697,577 to Forkner, U.S. Pat. No. 6,371,909 to Hoeg, et al., U.S. Pat. No. 6,500,115 to Krattiger et al., and WIPO Publication No. WO 01/22865 by Ramsbottom, as well as the pan-tilt videoendoscope design, such as is disclosed in U.S. Pat. No. 5,762,603 to Thompson. These designs rely on two mechanical degrees of freedom for changing the endoscopic line of sight, as is further explained below.

Figure 1:
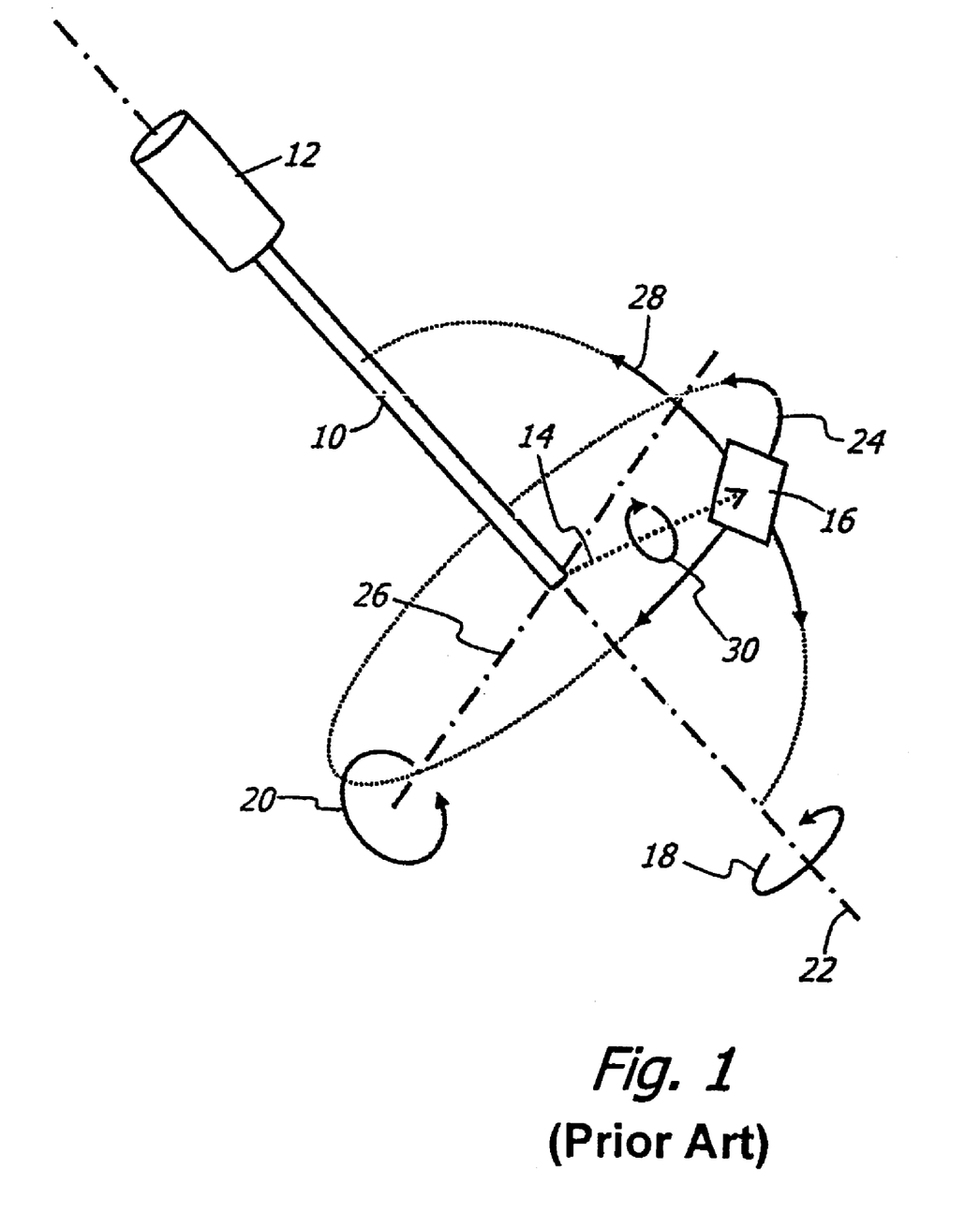
FIG. 1 is a schematic view of the operating principles of a variable direction of view endoscope.

The operating principles of such a scope are illustrated schematically in FIG. 1. A variable direction of view endoscope includes an endoscope shaft 10 with a proximal end 12. Such an endoscope has a view vector 14 with an attendant view field 16 having at least two degrees of freedom 18, 20. The first degree of freedom 18 permits rotation of the view vector 14 about the longitudinal axis 22 of the shaft 10, which allows the view vector 14 to scan in a latitudinal direction 24. The second degree of freedom 20 permits rotation of the view vector 14 about an axis 26 perpendicular to the longitudinal axis 22, which allows the view vector 14 to scan in a longitudinal direction 28. A third degree of freedom 30 may also be available because it is usually possible to adjust the rotational orientation of the endoscopic image.

Figure 2A:
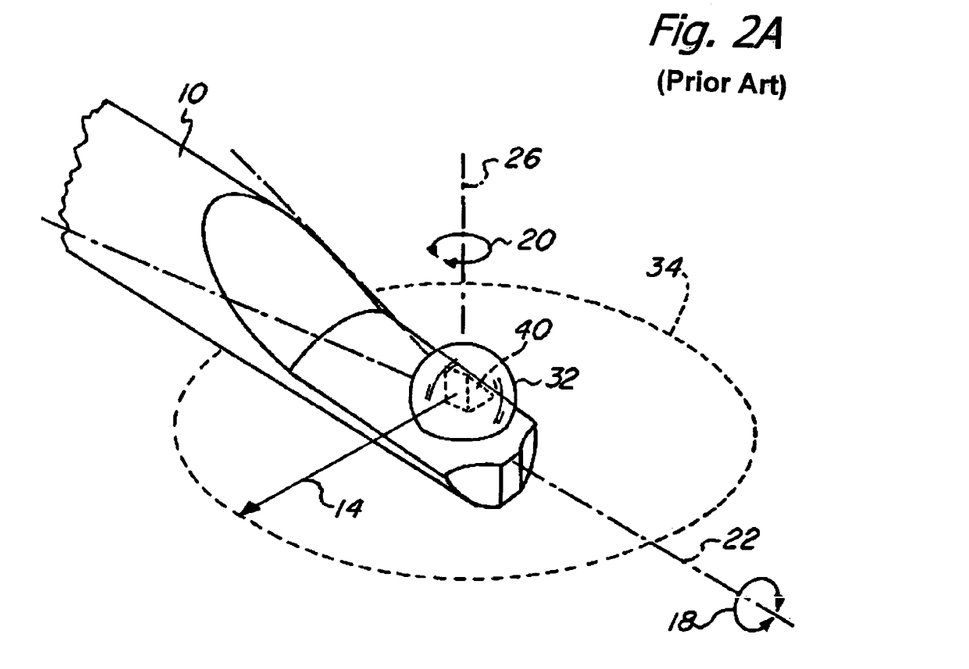
FIG. 2A is a perspective view of the distal end of the endoscope of FIG. 1.
Figure 2B:
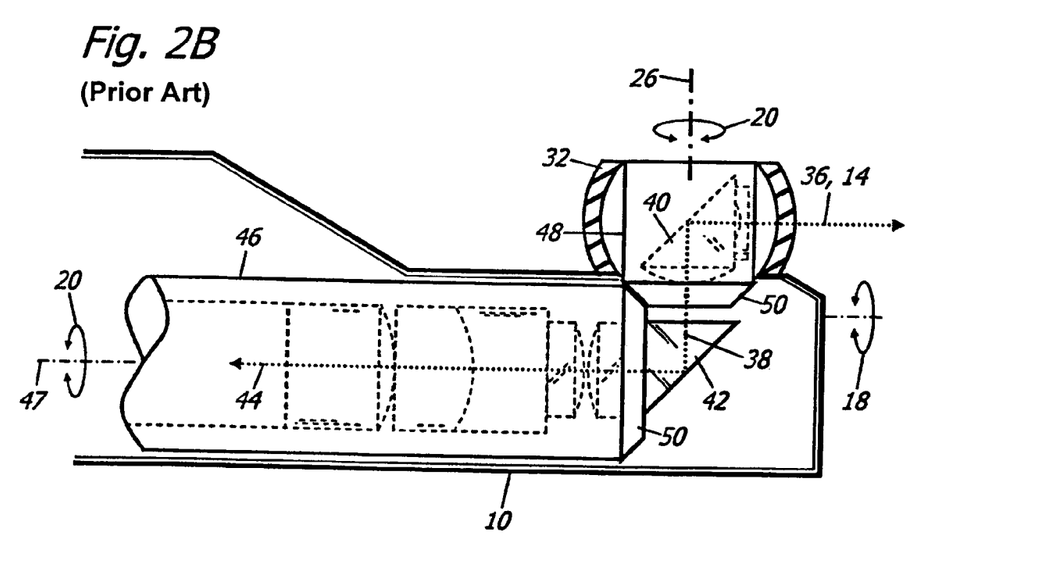
FIG. 2B is a side view in partial cross-section of the distal end of the endoscope of FIG. 2A.

Referring to FIGS. 2A-B, the operating principles of a typical variable direction of view instrument—namely, a dual prism scope—are illustrated. As shown in FIG. 2A, a right-angled prism 40, housed in a spherical viewing window 32, can rotate about the axis 26, representing the second degree of freedom 20. Accordingly, the view vector 14 sweeps in the longitudinal direction 28, resulting in an effective viewing range 34. As shown in FIG. 2B, the rotatable prism 40 refracts incoming light along a path 38 to a second, non-rotating prism 42, which delivers the light to an optical relay system, housed by a hollow transmission shaft 46, along a path 44. As noted, the first prism 40 rotates about the axis 26 and can be actuated by the transmission shaft 46 via a gear 50 in order to cause the view vector 14 to scan the viewing range 34 (i.e., the plane normal to the page).

As endoscopes have become more sophisticated, they have increasingly begun to include more on-board instrumentation, such as sensors and actuators. For example, in addition to image sensors, endoscopes have been proposed that include thermal sensors and pressure sensors. Pneumatic, piezoelectric, or electromagnetic actuators are also being incorporated into endoscopes for various purposes, such as mechanical zooming, automated scope insertion, retraction, rotation, and gravity camera stabilization, such as is disclosed in U.S. Pat. No. 6,097,423 to Mattsson-Boze et al.

Actuators can also be used to change the viewing direction of a variable direction of view instrument, as is further explained herein. As endoscopes gradually become more integrated with computers, automated actuation becomes more interesting because the computers can be used to control the endoscopic viewing direction, such as in the system disclosed in U.S. Pat. No. 6,663,559 to Hale et al. Accordingly, the changing endoscopic line of sight in such variable direction of view instruments is suitable for computer control through appropriately integrated actuators.

What is desired, therefore, is an actuation system that can control motion through at least two degrees of freedom in a variable direction of view instrument. What is further desired is an actuation system that does not require a lot of space or complex construction and assembly. What is also desired is an actuation system that limits transmission backlash and the need for unnecessary support bearings.

SUMMARY OF THE INVENTION

Accordingly, it is an object of the present invention to provide an instrument with a variable direction of view where multiple degrees of freedom can be controlled by an on-board system.

It is a further object of the present invention to provide an instrument with a variable direction of view that is compact.

It is yet another object of the present invention to provide an instrument with a variable direction of view providing simple construction and assembly.

In order to overcome the deficiencies of the prior art and to achieve at least some of the objects and advantages listed, the invention comprises a viewing instrument with a variable direction of view, including a proximal portion, an outer shaft extending out from the proximal portion, the shaft having a distal end and a first longitudinal axis, a view changing element arranged at the distal end of the outer shaft, an inner shaft at least partly disposed in the outer shaft that moves the view changing element, the inner shaft having a second longitudinal axis, first and second actuators arranged in the proximal portion, wherein the outer shaft is rotated about the first longitudinal axis by the first actuator and the inner shaft is rotated about the second longitudinal axis by the second actuator.

In another embodiment, the invention comprises a viewing instrument with a variable direction of view, including an outer shaft having a distal end, an inner shaft at least partly disposed in the outer shaft, a viewing element located at the distal end of the outer shaft and driven by the inner shaft, the viewing element having a variable view vector with first and second degrees of freedom, a first actuator coupled to the outer shaft for rotating the outer shaft such that the view vector pivots through the first degree of freedom, a second actuator coupled to the inner shaft for rotating the inner shaft such that the view vector pivots through the second degree of freedom.

In yet another embodiment, the invention comprises a viewing instrument with a variable direction of view, including an outer shaft having a distal end and a first longitudinal axis, an inner shaft at least partly disposed in the outer shaft, the inner shaft having a second longitudinal axis, a viewing element located at the distal end of the outer shaft, the viewing element having a rotational axis angularly offset from the first longitudinal axis and about which the viewing element is rotated by the inner shaft, a first actuator coupled to the outer shaft for rotating the outer shaft about the first longitudinal axis, a second actuator coupled to the inner shaft for rotating the inner shaft about the second longitudinal axis such that the viewing element rotates about the rotational axis.

In still another embodiment, the invention comprises a viewing instrument with a variable direction of view, including an instrument shaft having a distal end and a first longitudinal axis, a view changing element arranged at the distal end of the shaft, a transmission shaft at least partly disposed in the instrument shaft and having a second longitudinal axis, wherein the transmission shaft is coupled to the view changing element such that rotation of the transmission shaft about the longitudinal axis moves the view changing element, a first on-board actuator coupled to the instrument shaft for rotating the instrument shaft about the first longitudinal axis, and a second on-board actuator coupled to the transmission shaft for rotating the transmission shaft about the second longitudinal axis.

In some of these embodiments, the inner and outer shafts are coaxial, such that the first and second longitudinal axes are generally coincident, and in some embodiments, the rotational axis of the viewing element is substantially perpendicular to these axes.

In certain embodiments, the first and second actuators are first and second motors. In some of these embodiments, the motors are coaxial with the outer shaft. In others of these embodiments, a first gear is coupled to the first motor and rotated thereby and a second gear is driven by the first gear and coupled to the outer shaft such that the outer shaft is rotated by rotation of the second gear, while a third gear is coupled to the second motor and rotated thereby and a fourth gear is driven by the third gear and coupled to the inner shaft such that the inner shaft is rotated by rotation of the fourth gear.

In some embodiments, the instrument comprises a generally tubular member and a support assembly disposed in the tubular member, and the motors are mounted to the support assembly.

DETAILED DESCRIPTION OF THE INVENTION

Figure 3:
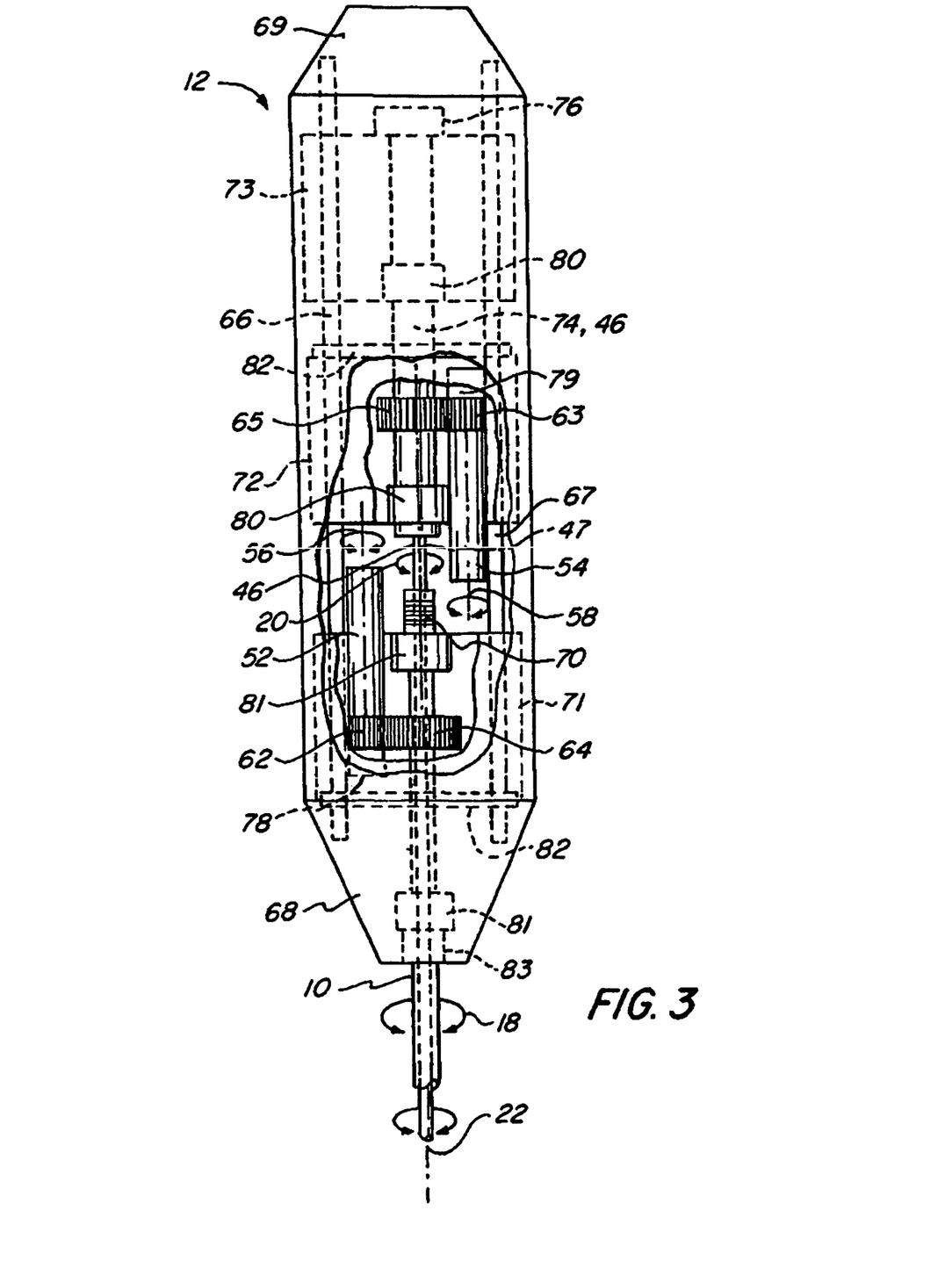
FIG. 3 is a partially cut-away, top plan view of a viewing instrument in accordance with the invention.

The basic components of one embodiment of an on-board actuation system for an instrument with a variable direction of view in accordance with the invention are illustrated in FIGS. 2-3. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

Referring first to FIGS. 2A-B, which illustrate the specific optics that may be employed, a right-angled prism 40, which is housed in a spherical viewing window 32 and receives incoming light, rotates about a rotational axis 26 angularly offset from, and in certain advantageous embodiments, perpendicular to, the longitudinal axis 22 of the outer endoscope shaft 10. Light travels through the optical transmission system in three paths: a first optical path segment 36, which is coincident with the view vector 14, a second path segment 38 optically coupling the rotatable right-angled prism 40 and a fixed right-angled prism 42, and a third optical path segment 44 coupling the fixed prism 42 to an imager 76 through an optical relay system. The optical relay system is housed in a tube 46, which also serves as a drive shaft, which is disposed inside the outer endoscope shaft 10. The drive shaft 46 transmits rotational motion about the drive shaft axis 47 into a perpendicular rotational motion (representing the second degree of freedom 20) by causing rotation of the prism 40, which is housed in a short tube 48, via a gear set 50. Also rotating the endoscope shaft 10 through the first degree of freedom 18 by rotating it about its longitudinal axis 22 makes it possible to point the view vector 14 in any direction.

As shown in FIG. 3, the outer endoscope shaft 10 and the inner drive shaft 46 are actuated by first and second actuators, such as first and second motors 52, 54, respectively. The first motor 52 and a second motor 54 are housed inside the proximal end 12 of the instrument, which may comprise a generally tubular member. The motors 52, 54 have axes 56, 58, respectively that are generally parallel to each other and to the endoscope longitudinal axis 22, which, at the proximal end, is generally coincident with the rotational axis 47 of the shaft 46. Rotational motion from the motors 52, 54 is transmitted into motion through the first and second degrees of freedom 18, 20 by rotating the outer and inner shafts 10, 46 via two sets of spur gears 62, 64, and 63, 65, respectively.

Figure 4:
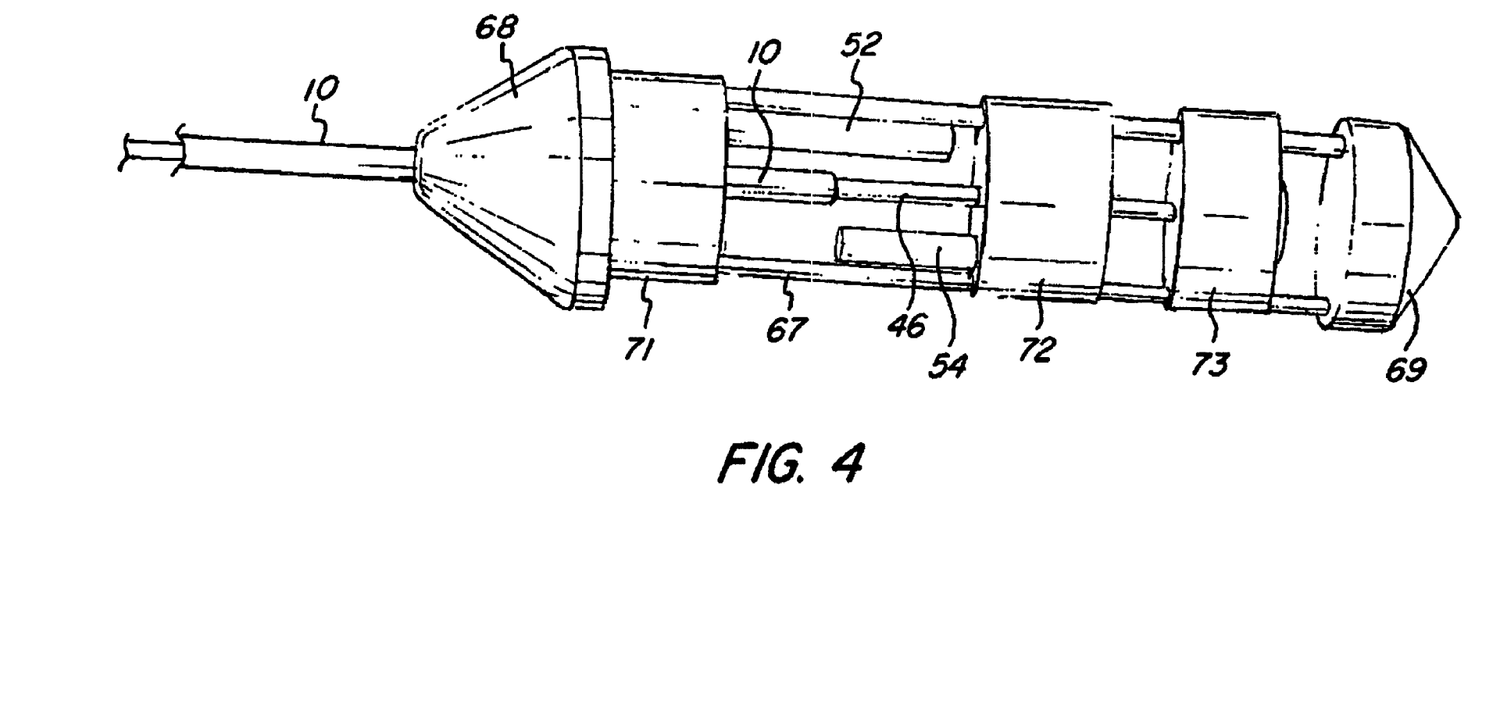
FIG. 4 is a partially exposed, perspective view of the viewing instrument of FIG. 3.

As previously noted, the proximal end 12 comprises a generally tubular housing, and a support assembly is disposed therein. Referring to FIGS. 3-4, this support assembly may, for example, comprise a framework including two high-strength rails 66, 67 anchored in front and back end caps 68, 69. A series of bulkheads 71, 72, 73 are located on the structural rails 66, 67, and the motors 52, 54 are mounted thereto. This support assembly may also, for example, further hold an electrical slip ring 70 for providing power to an LED illumination system (not shown), a proximal optics tube 74, and an electronic image sensor 76. The optics tube 74 is rigidly mated to the optomechanical drive shaft 46 and can be thought of as part of the shaft 46.

The transmission drive gears 62, 63 are mounted on the motor shafts, which are structurally supported by bearings 78, 79. Both the endoscope shaft 10 and the drive shaft 46 have driven gears 64, 65 and are supported by two sets of bearings 80, 81 on either side of the gears 64, 65 for structural rigidity and robustness. Rotations through the first and second degrees of freedom 18, 20 are monitored by a set of encoders 82. The encoders 82 are mounted on the shafts 10, 46, rather than on the motor shafts, so that rotation can be monitored directly and not across the transmission gears 62, 63, 64, 65, which have backlash. An O-ring 83 seals the interface between the rotating endoscope shaft 10 and the stationary proximal housing 12.

Figure 5:
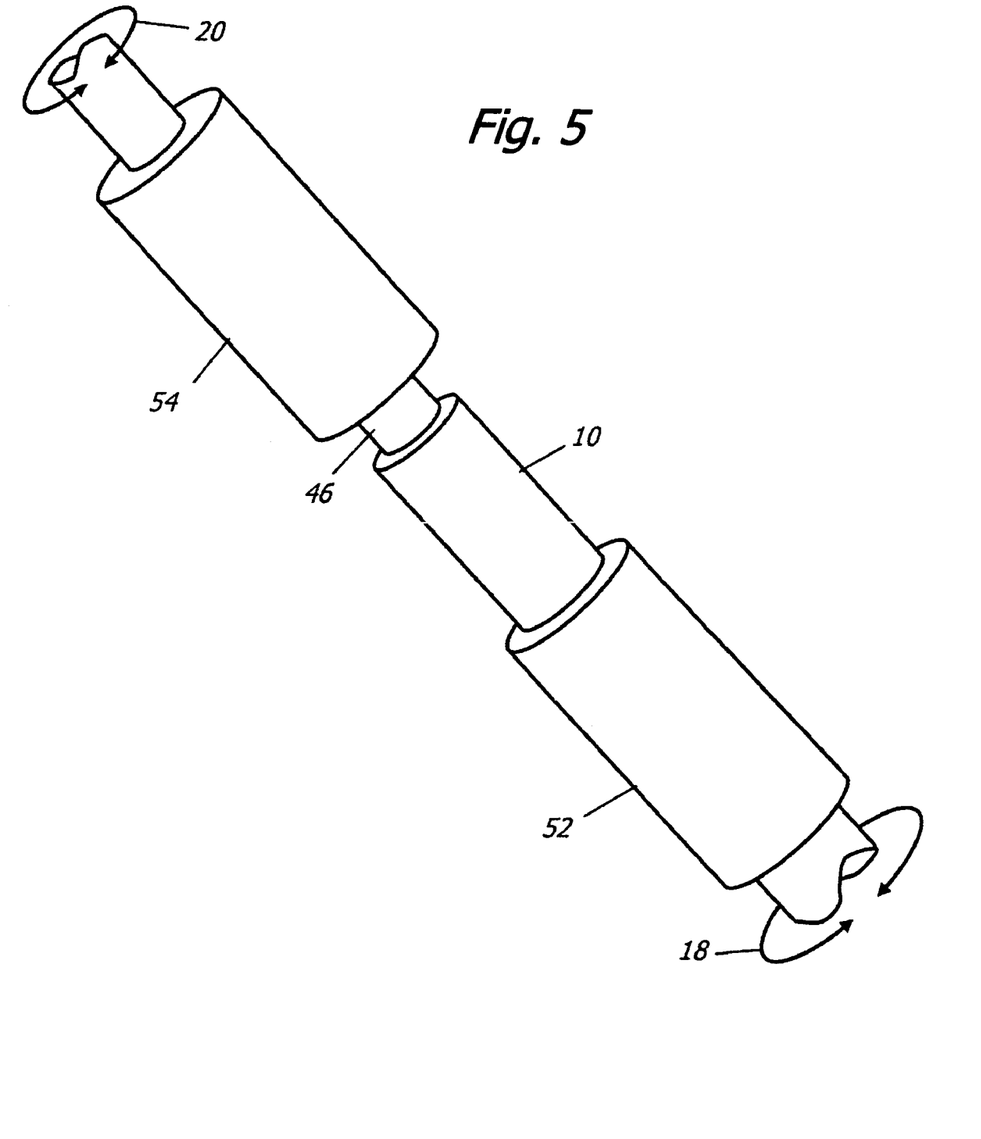
FIG. 5 is a perspective view of a concentric direct-drive assembly for use in the viewing instrument of FIG. 3.

Depending on the particular requirements of the application in which the invention is being implemented, it may also be desirable to employ other arrangements of the motors 52, 54. For example, direct-drive motors, which have hollow centers, may be used, as illustrated in FIG. 5. This makes it possible to pass the optomechanical transmission shaft 46 through the centers of both motors 52, 54 to reach the proximal image sensor 76. Such an arrangement provides several advantages, including the fact that the motors 52, 54 can both be mounted coaxially with the drive shaft 46, requiring fewer parts and less space and making the design easier to build, assemble, and align, and also the fact that both the drive shaft 46 and the endoscope shaft 10 can be driven directly without the need for transmission gears and separate encoder wheels mounted on the shafts, thereby reducing backlash.

Figure 6:
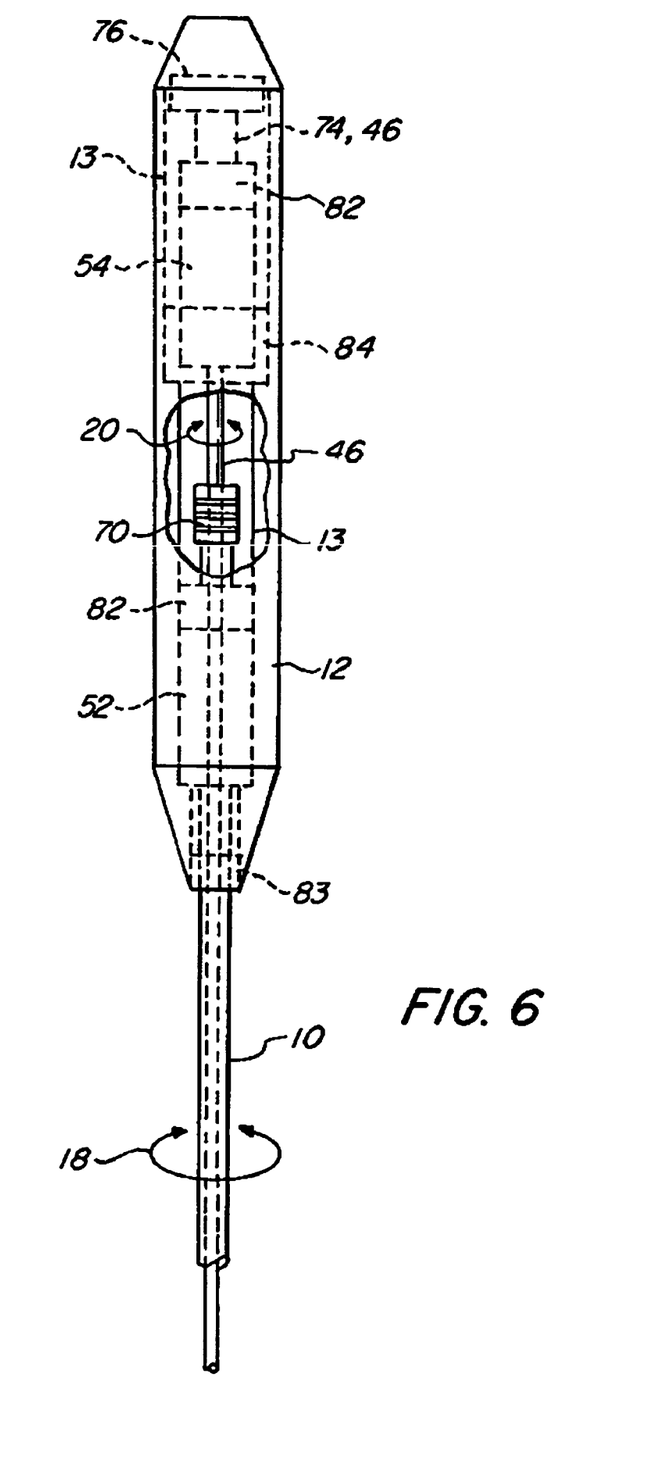
FIG. 6 is a top plan view of a viewing instrument employing the direct drive assembly of FIG. 5.

As shown in FIG. 6, in this type of system, the motors 52, 54 are housed in a single bored-out proximal superstructure 12, which serves as both the structural support and the external shell. While the first motor 52 is mounted directly to an internal wall 13 of the superstructure 12, the second motor 54 is connected to the interior of the superstructure 12 through a mounting bracket 84. The optomechanical transmission shaft 46 passes through the center of both motors 52, 54 and is attached to a tube 74, which houses optics coupling the relay system and the camera 76. All shaft-bearings are integral to the motors 52, 54, making external bearings unnecessary. The rotational position encoders 82 are also built onto the motors 52, 54, and thus, conveniently monitor the positions of the endoscope and drive shafts 10, 46 directly. Control-electronics and wiring for the camera 76 and motors 52, 54 can either be incorporated into the superstructure 12 or housed in a separate box. It should be noted that many variations of the mounting schemes and structural configurations are possible.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A viewing instrument with a variable direction of view, comprising:
    a proximal portion;
    an outer shaft extending out from said proximal portion, said shaft having a distal end and a first longitudinal axis about which said outer shaft rotates;
    an inner shaft at least partly disposed in said outer shaft and having a second longitudinal axis about which said inner shaft rotates that is generally coincident with the first longitudinal axis;
    a view changing element located at the distal end of said outer shaft, said view changing element having a rotational axis angularly offset from said first longitudinal axis and about which said viewing element is rotated by said inner shaft;
    first and second actuators arranged in said proximal portion, wherein said outer shaft is rotated about the first longitudinal axis by said first actuator and said inner shaft is rotated about the second longitudinal axis by said second actuator such that said viewing element rotates about said rotational axis.

2. The viewing instrument of claim 1, wherein said view changing element has a rotational axis substantially perpendicular to said first longitudinal axis.

3. The viewing instrument of claim 1, wherein said first and second actuators comprise first and second motors.

4. The instrument of claim 3, wherein said first and second motors have rotational axes that are substantially parallel.

5. The instrument of claim 3, further comprising:
    a first gear coupled to said first motor and rotated thereby;
    a second gear driven by said first gear and coupled to said outer shaft such that said outer shaft is rotated by rotation of said second gear;
    a third gear coupled to said second motor and rotated thereby; and
    a fourth gear driven by said third gear and coupled to said inner shaft such that said inner shaft is rotated by rotation of said fourth gear.

6. The viewing instrument of claim 3, wherein said first and second motors are coaxial with said outer shaft.

7. The viewing instrument of claim 1, wherein said proximal portion comprises:
    a generally tubular member; and
    a support assembly disposed in said tubular member, wherein said actuators are mounted to said support assembly.

8. The viewing instrument of claim 1, wherein said view changing element comprises a right-angled prism.

9. The viewing instrument of claim 1, wherein said outer shaft comprises an endoscope shaft.

10. A viewing instrument with a variable direction of view, comprising:
    an outer shaft having a distal end and a first longitudinal axis about which said outer shaft rotates;
    an inner shaft at least partly disposed in said outer shaft, said inner shaft having a second longitudinal axis about which said inner shaft rotates that is generally coincident with the first longitudinal axis;
    a viewing element located at the distal end of said outer shaft, said viewing element having a rotational axis angularly offset from said first longitudinal axis and about which said viewing element is rotated by said inner shaft;
    a first actuator coupled to said outer shaft for rotating said outer shaft about said first longitudinal axis;
    a second actuator coupled to said inner shaft for rotating said inner shaft about said second longitudinal axis such that said viewing element rotates about said rotational axis.

11. The viewing instrument of claim 10, wherein said rotational axis is substantially perpendicular to said first longitudinal axis.

12. The viewing instrument of claim 10, wherein said first and second actuators comprise first and second motors.

13. The instrument of claim 12, wherein said first and second motors have rotational axes that are substantially parallel.

14. The instrument of claim 12, further comprising:
    a first gear coupled to said first motor and rotated thereby;
    a second gear driven by said first gear and coupled to said outer shaft such that said outer shaft is rotated by rotation of said second gear;
    a third gear coupled to said second motor and rotated thereby; and a fourth gear driven by said third gear and coupled to said inner shaft such that said inner shaft is rotated by rotation of said fourth gear.

15. The viewing instrument of claim 12, wherein said first and second motors are coaxial with said outer shaft.

16. The viewing instrument of claim 12, further comprising:
a generally tubular member; and
a support assembly disposed in said tubular member, wherein said motors are mounted to said support assembly.

17. The viewing instrument of claim 10, wherein said viewing element comprises a right-angled prism.

18. The viewing instrument of claim 10, wherein said outer shaft comprises an endoscope shaft.

19. A viewing instrument with a variable direction of view, comprising:
an instrument shaft having a distal end and a first longitudinal axis;
a view changing element arranged at the distal end of said shaft and having a rotational axis;
a transmission shaft at least partly disposed in said instrument shaft and having a second longitudinal axis generally coincident with the first longitudinal axis, wherein said transmission shaft is coupled to said view changing element such that rotation of said transmission shaft about the second longitudinal axis rotates said view changing element about said rotational axis;
a first on-board actuator coupled to said instrument shaft for rotating said instrument shaft about said first longitudinal axis; and
a second on-board actuator coupled to said transmission shaft for rotating said transmission shaft about said second longitudinal axis such that said viewing element rotates about said rotational axis.

20. The viewing instrument of claim 19, wherein said view changing element has a rotational axis substantially perpendicular to said second longitudinal axis and about which said element rotates when said transmission shaft rotates about said second longitudinal axis.

* * * * *